United States Patent [19]

Kosóczky et al.

[11] 3,988,461
[45] Oct. 26, 1976

[54] PHARMACEUTICAL COMPOSITION FOR THE TREATMENT OF PARKINSON'S DISEASE

[75] Inventors: Ibolya Kosóczky; Zoltán Budai; Lászlo Kósa; Lujza Petócz, all of Budapest, Hungary

[73] Assignee: Egyt Gyogyszervegyeszeti Gyar, Budapest, Hungary

[22] Filed: June 5, 1975

[21] Appl. No.: 583,904

[30] Foreign Application Priority Data
June 13, 1974 Hungary............................ EE 2244

[52] U.S. Cl.................................. 424/267; 424/319
[51] Int. Cl.² ............... A61K 31/195; A61K 31/445
[58] Field of Search............................ 424/319, 267

[56] References Cited
UNITED STATES PATENTS
3,014,911  12/1961  Engelhardt.................... 260/293.62

OTHER PUBLICATIONS

Modell, Drugs in Current Use and New Drugs, p. 35, (1973).

Primary Examiner—Stanley J. Friedman
Attorney, Agent, or Firm—Karl F. Ross; Herbert Dubno

[57] ABSTRACT

Pharmaceutical compositions for the treatment of Parkinson's Disease contain 5-(1-methylpiperidylidene-4-5H-dibenzo(a,d)cycloheptene or a pharmaceutically acceptable salt thereof and L-3,4-dihydroxyphenylalanine or a pharmaceutically acceptable salt thereof in a weight ratio of 0.5–5 : 50–150, optionally together with a carrier.

1 Claim, No Drawings

PHARMACEUTICAL COMPOSITION FOR THE TREATMENT OF PARKINSON'S DISEASE

The invention relates to new pharmaceutical compositions having antiparkinson effects, containing as active agents L-3,4-dihydroxyphenylalanine (L-Dopa) or a pharmaceutically acceptable salt thereof and 5-(1-methylpiperidylidene-4-5H -dibenzo- (a,d)cycloheptene (Cyproheptadine) or a pharmaceutically acceptable salt thereof.

L-Dopa is an antiparkinson agent extensively used in clinical practice. This compound possesses, however, several side effects, including a locomotive stimulant effect, a sedative effect and an anorexigenic-effect.

Cyproheptadine is also widely used in the therapy, primarily as an anti-allergic substance. This compound possesses oxerigenic effect as well.

Now it has been found that L-Dopa, when administered in combination with Cyproheptadine, exerts an increased antiparkinson effect surpassing significantly the sum of the effects of the individual components. It has been found, furthermore, that the synergistic increase of the antiparkinson activity is not accompanied by a synergistic increase in toxicity, i.e. the toxicity of the composition containing the above two active agents is approximately equal to the sum of the toxicities of the individual components. A further significant advantage is that the undesired side effects of L-Dopa are suppressed to a great extent in the presence of Cyproheptadine.

The synergistic increase in the antiparkinson effect was investigated by studying the inhibition of Oxotremorine-induced tremor and the antagonism of Perphenazine-induced catalepsy.

1. Inhibition of Oxotremorine-induced Tremor

The tests were performed on mice of both sexes, each weighing 20 to 30 g. The groups consisted of 20 animals each. The test animals were treated orally with varying amounts of Cyproheptadine hydrochloride or L-Dopa, respectively. 30 minutes after the introduction of the active agents, the animals were treated with Oxotremorine [1-(4-/1-pyrrolidinyl/-2-butinyl)-2-pyrrolidinone], and the $ED_{50}$ values of the active agents were determined. According to the above test $ED_{50} = 3$ mg./kg. for Cyproheptadine hydrochloride, and $ED_{50} < 1200$ mg./kg. for L-Dopa.

To study the interaction of the two active agents, the animals were treated with 200 mg./kg. of L-Dopa (less than one-fourth of the $ED_{50}$ value). 30 minutes after the administration of L-Dopa, varying amounts of Cyproheptadine hydrochloride were introduced, and after further 30 minutes the animals were treated with a standard dosage of Oxotremorine. The results of this test are summarized in Table 1.

Table 1

| Compound | Dosage mg./kg. | No. of animals | Inhibition, % |
|---|---|---|---|
| Cyproheptadine HCl | 0.2 | 20 | 0 |
| | 0.4 | 20 | 20 |
| | 0.8 | 20 | 50 |
| | 1.6 | 20 | 90 |

$ED_{50} = 0.7 (0.98 - 0.5)$ mg./kg. p.o.

In a further series of tests the animals were treated with 1 mg./kg. of Cyproheptadine hydrochloride. 30 minutes after the administration of Cyproheptadine hydrochloride, L-Dopa was introduced in varying amounts, and after a further period of 30 minutes the animals were treated with a standard dosage of Oxotremorine. The results of this test are summarized in Table 2.

Table 2

| Compound | Dosage mg./kg. | No. of animals | Inhibition, % |
|---|---|---|---|
| L-Dopa | 50 | 10 | 15 |
| | 100 | 20 | 52.5 |
| | 200 | 20 | 67.5 |
| | 400 | 20 | 85 |

$ED_{50} = 120 (180 - 80)$ mg./kg. p.o.

The expected $ED_{50}$ values were determined by constructing an isobole, and the expected values were compared to the observed ones. The results of this comparison are given in Table 3.

Table 3

| Pre-treatment | Treatment | $ED_{50}$ mg./kg. calculated | found | Difference |
|---|---|---|---|---|
| 200 mg./kg. of L-Dopa | Cyproheptadine hydrochloride | 1.45 | 0.7 | +107 |
| 1 mg./kg. of Cyproheptadine HCl | L-Dopa | 260 | 120 | +117 |

The percentage deviations prove unambiguously that each of the active agents synergistically increases the effects of the other.

2. Antagonism of Perphenazine-induced Catalepsy

The tests were performed on white rats of both sexes, each weighing 150 to 200 g. The animals were treated orally with varying amounts of Cyproheptadine hydrochloride or L-Dopa, respectively, and 30 minutes after the introduction of the active agents the animals were treated with a standard dosage of Perphenazine [2-chloro-10-(3-/4-(2-hydroxy-ethyl)-1-piperazinyl/-propyl)-phenothiazine]. The percentage of catalepsy inhibition was examined as a function of the time. The results of these tests are summarized in Table 4.

Table 4

| Compound | Dosage mg./kg. | No. of animals | Percentage inhibition after | | | | |
|---|---|---|---|---|---|---|---|
| | | | 0.5 | 1 | 2 | 3 | 4 hours |
| Cyproheptadine hydrochloride | 5 | 10 | 47 | 49 | 0 | 4 | — |
| | 10 | 10 | 89 | 72 | 61 | 57 | — |
| | 20 | 10 | 76 | 77 | 73 | 59 | — |
| L-Dopa | 100 | 10 | 2 | 15 | 18 | 18 | 10 |
| | 200 | 10 | 0 | 23 | 23 | 3 | 5 |
| | 400 | 10 | 27 | 33 | 32 | 20 | 10 |

Interaction of Cyproheptadine hydrochloride and L-Dopa in the Perphenazine-catalepsy test:

The interaction of the active agents was studied on white rats, according to the method described above. Cyproheptadine hydrochloride was administered in oral dosages of 2 or 4 mg./kg., respectively. 30 minutes after the introduction of Cyproheptadine hydrochloride the animals were treated with varying amounts of L-Dopa, and after an additional period of 30 minutes the animals were treated with a standard dosage of Perphenazine. The results of this test are summarized in Table 5.

Table 5

| Compound | Dosage mg./kg. | No. of animals | Percentage inhibition after | | | | |
|---|---|---|---|---|---|---|---|
| | | | 0.5 | 1 | 2 | 3 | 4 hours |
| Cyproheptadine HCl | 2 | 10 | 37 | 8 | 14 | 8 | — |
| Cyproheptadine HCl +L-Dopa | 2 50 | 20 | 24 | 29 | 24 | 24 | 2 |
| Cyproheptadine HCl +L-Dopa | 2 100 | 30 | 41 | 34 | 21 | 11 | 21 |
| Cyproheptadine HCl +L-Dopa | 2 200 | 20 | 56 | 58 | 56 | 53 | 33 |
| Cyproheptadine HCl | 4 | 20 | 20 | 10 | 14 | 18 | — |
| Cyproheptadine HCl +L-Dopa | 4 50 | 20 | 15 | 18 | 8 | 8 | 5 |
| Cyproheptadine HCl +L-Dopa | 4 100 | 20 | 55 | 53 | 45 | 33 | 36 |
| Cyproheptadine HCl +L-Dopa | 4 200 | 20 | 82 | 70 | 73 | 73 | 66 |

The above data clearly indicate the synergistic increase of the activities of the individual active agents.

3. Toxicity Tests

The toxicities of the individual components were determined separately on mice. The active agents were suspended in water containing Tween 80, and the suspension was administered orally to the animals in a dosage of 20 ml./kg. The animals were kept under observation for 72 hours. The poisoned animals perished within 48 hours.

On the basis of the above test the $LD_{50}$ values of the individual active agents are as follows:

Cyproheptadine hydrochloride: 135 mg./kg., and L-Dopa: 4.2 g./kg.

The joint toxicity of the individual active agents was determined as follows:

a. The animals were treated with 1 g/kg. of L-Dopa. 1 hour after the administration of L-Dopa, the animals were treated with varying amounts of Cyproheptadine hydrochloride. The results of this test are summarized in Table 6a.

Table 6a

| Compound | Dosage mg./kg. | Perished animals/ treated animals | Perishment, % |
|---|---|---|---|
| Cyproheptadine HCl | 90 | 2/20 | 10 |
| | 135 | 7/20 | 35 |
| | 200 | 14/20 | 70 |
| | 300 | 19/20 | 95 | b. The animals were treated with 2 g./kg. of L-Dopa, and varying amounts of Cyproheptadine hydrochloride were administered subsequently. The results of this test are summarized in Table 6b.

Table 6b

| Compound | Dosage mg./kg. | Perished animals/ treated animals | Perishment, % |
|---|---|---|---|
| Cyproheptadine HCl | 60 | 0/20 | 0 |
| | 90 | 2/20 | 10 |
| | 135 | 8/20 | 40 |
| | 200 | 17/20 | 85 | c. The animals were treated with 3 g./kg. of L-Dopa, and subsequently Cyproheptadine hydrochloride was administered in varying amounts. The results of this test are summarized in Table 6c.

Table 6c

| Compound | Dosage mg./kg. | Perished animals/ treated animals | Perishment, % |
|---|---|---|---|
| Cyproheptadine HCl | 40 | 1/20 | 5 |
| | 60 | 5/20 | 25 |
| | 90 | 9/20 | 45 |
| | 135 | 16/20 | 80 |
| | 200 | 15/20 | 75 |

The above data indicate that the pre-treatments with 1 and 2 g./kg. of L-dopa, respectively, hardly influence the toxicity of Cyproheptadine hydrochloride, consequently the two active agents do not potentiate the toxicities of each other.

In order to evaluate the changes in toxicity, the expected toxicities of the compositions listed below were determined by constructing an isobole, and the calculated data were compared to the observed ones. The results are summarized in Table 7.

Table 7

| Combination | Dosage | Perished animals/ treated animals | Perishment, % | |
|---|---|---|---|---|
| | | | expected | found |
| L-Dopa + Cyproheptadine HCl | 1 g./kg. 105 mg/kg. | 8/20 | 50 | 40 |
| L-Dopa + Cyproheptadine HCl | 2 g./kg. 75 mg/kg. | 8/20 | 50 | 40 |
| L-Dopa + Cyproheptadine HCl | 3 g./kg. 45 mg/kg. | 12/20 | 50 | 60 |

Based on the above data it can be stated that the joint toxicity of the two active agents is the sum of the individual toxicities of the respective ingredients.

4. Examination of Side Effects:

The side effects of the individual active agents as well as those of the compositions were examined as follows:

a. Examination of Sedative Effects on Mice, According to the Hexobarbital Narcosis Test

The compounds to be tested were suspended in water containing Tween 80, and 20 ml./kg. dosages of the obtained suspensions were administered orally to the test animals. 1 hour after this treatment 40 mg./kg. of hexobarbital [5-(1-cyclohexenyl)-1,5-dimethylbarbituric acid] were administered intravenously to the animals, and the duration of sleep was observed. The results were graded as positive when the sleeping period of the test animals was higher by at least 150% than the average value determined for the control group.

The results of the above test are summarized in Table 8.

Table 8

| Compound | Dosage mg./kg. | Positive animals/ treated animals | % |
|---|---|---|---|
| Cyproheptadine HCl | 2.5 | 6/18 | 33 |
| | 5.0 | 4/6 | 66 |
| | 10.0 | 5/6 | 83 |
| L-Dopa | 520 | 0/12 | 0 |
| | 800 | 1/6 | 16.6 |
| | 1200 | 5/6 | 83 |
| L-Dopa + Cyproheptadine HCl | 520 2.5 | 5/20 | 25 |

From the data of this Table it can be concluded that the tested compounds do not potentiate the sedative effects on each other in the dosages indicated.

b. Examination of Locomotive Stimulating Effect on Motility Test

It has been examined how Cyproheptadine hydrochloride influences the locomotive stimulating effect, characteristic of L-Dopa, in the combination according to the invention. The tests were performed on white mice. An intraperitoneal dosage of 500 mg./kg. of L-Dopa was administered 30 minutes after the pre-treatment with Cyproheptadine hydrochloride. The results of the above test are given in Table 9.

Table 9

| Substance | Dosage mg./kg. | Manner of administration | Average No. of light interruptions | Change % |
|---|---|---|---|---|
| Physiological saline | — | p.o. | | |
| Physiological saline | — | i.p. | 227 | — |
| Cyproheptadine HCl + physiological saline | 2.5 — | p.o. i.p. | 145 | −36 |
| Physiological saline + L-Dopa | — 500 | p.o. i.p. | 465 | +105 |
| Cyproheptadine HCl + L-Dopa | 2.5 500 | p.o. i.p. | 437 | +93 |

No synergistic increase of the locomotive stimulating effect was observed, i.e. in the tested dosages Cyproheptadine hydrochloride does not influence the locomotive stimulating effect of L-Dopa.

Thus the invention relates to pharmaceutical compositions containing Cyproheptadine or a pharmaceutically acceptable salt thereof, and L-Dopa or a pharmaceutically acceptable salt thereof in a weight ratio of 0.5–5 : 50–150. These pharmaceutical compositions may contain optionally other conventional pharmaceutical additives, such as carriers, diluents and auxiliary agents, and may be presented in any form suitable for oral, parenteral or rectal administration, such as capsules, tablets, coated tablets, emulsions, suspensions, injections, suppositories, etc.

The pharmaceutical compositions according to the invention are prepared by admixing Cyproheptadine or a pharmaceutically acceptable salt thereof with L-Dopa or a pharmaceutically acceptable salt thereof in a weight ratio of 0.5–5 : 50–150, and converting the obtained mixture into pharmaceutical compositions by methods known per se, optionally by utilizing other conventional pharmaceutical additives as defined above.

According to the invention one may also proceed by forming first granulates from the individual components, admixing these granulates with each other, and processing the obtained mixture into pharmaceutical compositions.

The orally administerable compositions suitable for the treatment of adult humans may contain about 1 to 3 mg. of Cyproheptadine and about 100 to 250 mg. of L-Dopa per dosage unit. This dosage is administered preferably thrice a day.

The compositions according to the invention, containing L-Dopa in admixture with Cyproheptadine, are much more suitable for the treatment of parkinsonism than the known compositions having L-Dopa as the only active ingredient. When administered alone, the optimum dosage of L-Dopa is 3 to 8 g. per day, whereas when administered in combination with Cyproheptadine, a daily dosage of 0.3 to 0.75 g. is already sufficient to reach the desired results. A further advantage is that in the pharmaceutical composition according to the invention the undesired side effects of L-Dopa are suppressed to a great extent.

The invention is elucidated by the aid of the following non-limiting Examples. The compositions according to the Examples contain Cyproheptadine in the form of its hydrochloride, it should be noted, however, that the free base or any other acid addition salt of Cyproheptadine can also be utilized.

EXAMPLE 1

Preparation of Tablets Each Weighing 200 mg.

Composition of one tablet:

| | | |
|---|---|---|
| a) | L-Dopa | 50.0 mg. |
| | Cyproheptadine hydrochloride | 3.0 mg. |
| | Lactose | 83.0 mg. |
| | Corn starch | 44.0 mg. |
| b) | Talc | 5.4 mg. |
| | Magnesium stearate | 0.6 mg. |
| | | 200.0 mg. |

The components listed under point a) are admixed with each other, the mixture is converted into granules by a method known per se, the obtained granules are dried at 40° to 42° C, and finally admixed with the components listed under point b). The mixture is compressed to form tablets each weighing 200 mg.

EXAMPLE 2

Preparation of Tablets Each Weighing 400 mg.

Composition of one tablet:

| | |
|---|---|
| L-Dopa | 200.0 mg. |
| Cyproheptadine hydrochloride | 4.0 mg. |
| Lactose | 98.0 mg. |
| Corn starch | 83.0 mg. |
| Ethyl cellulose | 10.0 mg. |
| Talc | 0.5 mg. |
| Magnesium stearate | 0.5 mg. |
| | 400.0 mg. |

The active ingredients are admixed with the magnesium stearate, the lactose and the corn starch, and the mixture is kneaded with a methylene chloride solution of the ethyl cellulose. The obtained mass is granulated, the granules are dried at 40° to 50° C, admixed with the talc, and the mixture is compressed into tablets each weighing 400.0 mg.

EXAMPLE 3

Preparation of Capsules

Composition of one capsule:

| | |
|---|---|
| L-Dopa | 50.0 mg. |
| Cyproheptadine hydrochloride | 2.0 mg. |
| Lactose | 33.0 mg. |
| Corn starch | 6.0 mg. |
| Talc | 4.0 mg. |
| | 95.0 mg. |

The active ingredients are blended with the starch and the lactose, the homogeneous mixture is sieved, then blended with the talc, and the mixture is filled into gelatine capsules.

What we claim is:

1. A pharmaceutical composition for the treatment of parkinsonism, containing 5-(1-methylpiperidylidene-4-5H-dibenzo(a,d)cycloheptene or a pharmaceutically acceptable salt thereof, and L-3,4-dihydroxyphenylalanine or a pharmaceutically acceptable salt thereof in a weight ratio of 0.5–5 : 50–150.

* * * * *